United States Patent
Gallardo Ruiz et al.

(10) Patent No.: US 10,988,591 B2
(45) Date of Patent: Apr. 27, 2021

(54) VINYL-LACTAM-BASED HYDROGEL COATINGS

(71) Applicants: Consejo Superior de Investigaciones Cientificas (CSIC), Madrid (ES); Universidad Complutense de Madrid, Madrid (ES)

(72) Inventors: Alberto Gallardo Ruiz, Madrid (ES); Juan Rodríguez Hernández, Madrid (ES); Helmut Reinecke, Madrid (ES); Carlos Elvira Pujalte, Madrid (ES); Carolina García Sánchez, Madrid (ES); Maria Eugenia Pérez Ojeda, Madrid (ES); Enrique Martínez Campos, Madrid (ES); Ana María Santos Coquillat, Madrid (ES); Ana Civantos Fernández, Madrid (ES)

(73) Assignees: Consejo Superior De Investigaciones Científicas (Csic); Universidad Complutense De Madrid

( * ) Notice: Subject to any disclaimer, the term of this patent is extended or adjusted under 35 U.S.C. 154(b) by 0 days.

(21) Appl. No.: 16/512,572

(22) Filed: Jul. 16, 2019

(65) Prior Publication Data

US 2020/0002494 A1    Jan. 2, 2020

Related U.S. Application Data

(63) Continuation of application No. PCT/ES2018/070029, filed on Jan. 16, 2018.

(30) Foreign Application Priority Data

Jan. 16, 2017   (ES) ............................... ES201730039

(51) Int. Cl.
  *C08J 7/18*    (2006.01)
  *C08F 2/48*    (2006.01)
  (Continued)

(52) U.S. Cl.
  CPC .................. *C08J 7/18* (2013.01); *C08F 2/48* (2013.01); *C08F 26/06* (2013.01); *C08K 5/11* (2013.01);
  (Continued)

(58) Field of Classification Search
  CPC ...... C08J 7/18; C08J 2325/06; C08J 2369/00; C08J 2377/00; C08J 2439/04; C08F 2/48;
  (Continued)

(56) References Cited

U.S. PATENT DOCUMENTS 3,532,679 A    10/1970   Steckler
4,058,491 A    11/1977   Steckler

OTHER PUBLICATIONS

Bora Lee et al., "initiated chemical vapor deposition of thermoresponsive poly(N-vinylcaprolactam) thin films for cell : sheet engineering"; Acta Biomater., Aug. 2013; 9(8): p. 7891-7698.*

(Continued)

*Primary Examiner* — William K Cheung
(74) *Attorney, Agent, or Firm* — Boyle Fredrickson, SC

(57) ABSTRACT

The invention relates to a material formed by a polymer substrate and a hydrogel based on vinyl-lactams and ionic methacrylates. The invention also relates to a method for producing this material and to the use thereof for cell culture and cell monolayer engineering, for preparing 3D scaffolds and manufacturing thermosensitive mechanical actuators.

31 Claims, 15 Drawing Sheets

(51) Int. Cl.
*C08F 26/06* (2006.01)
*C08K 5/11* (2006.01)
*C08L 25/06* (2006.01)
*C08L 69/00* (2006.01)
*C08L 77/00* (2006.01)
*C08K 5/3415* (2006.01)

(52) U.S. Cl.
CPC ........... *C08K 5/3415* (2013.01); *C08L 25/06* (2013.01); *C08L 69/00* (2013.01); *C08L 77/00* (2013.01); *C08J 2325/06* (2013.01); *C08J 2369/00* (2013.01); *C08J 2377/00* (2013.01); *C08J 2439/04* (2013.01)

(58) Field of Classification Search
CPC ......... C08F 26/06; C08K 5/11; C08K 5/3415; C08L 25/06; C08L 69/00; C08L 77/00
USPC ........................................................ 524/548
See application file for complete search history.

(56) References Cited

OTHER PUBLICATIONS

Bora Lee et al.; "Initiated chemical vapor deposition of thermoresponsive poly (N-vinylcaprolactam) thin films for cell sheet engineering"; Acta Biomater. Aug. 2013; 9(8): 7691-7698—(21) pages.

Boguang Yang et al.; "A thermoresponsive poly (N-vinylcaprolactam-co-sulfobetaine methacrylate) zwitterionic hydrogel exhibiting switchable anti-biofouling and cytocompatibility"; Royal Society of Chemistry, Polymer Chemistry, 2015, 6, 3431-3442; Mar. 17, 2015—(12) pages.

Inmaculada Aranaz et al.; "Pseudo-double network hydrogels with unique properties as supports for cell manipulation"; Royal Society of Chemistry, Journal of Materials Chemistry B, 2014, 2, 3839-3848; Apr. 11, 2014—(10) pages.

* cited by examiner (b)

↓ Small Swelling

Large amount of chains embedded in the support ↓ The hydrogel remains anchored at the PC surface

VINYL-LACTAM-BASED HYDROGEL COATINGS

CROSS-REFERENCE TO RELATED APPLICATIONS

This application is a continuation of and claims priority to PCT Application No. PCT/ES2018/070029, filed on Jan. 16, 2018, which, in turn, claims priority to Spanish Application No. P201730039, filed on Jan. 16, 2017. The entire contents of each of these applications is incorporated herein by reference.

BACKGROUND OF THE INVENTION

Field of the Invention

The invention relates to a product comprising a polymeric substrate and a hydrogel coating based on vinyl-lactams, with or without methacrylates, this coating has been anchored to the polymeric substrate. A hybrid interface has been formed between the substrate and the hydrogel as a result of the diffusion of hydrogel precursor molecules in the outer layers of the polymeric substrate. By controlling the experimental parameters, the hydrogel formed on the substrate can either remain intact or partially detach leaving the hybrid interface, that is, giving rise to a surface functionalized substrate that can be structured on said surface by the formation of wrinkles or other textures. This invention also relates to the application of these materials as supports for cell culture and engineering of cellular sheets (monolayers), preparation of 3D scaffolds and the manufacture of thermosensitive mechanical actuators.

Description of Related Art

The use of polymeric materials such as thermosensitive substrates based on poly-N-isopropylacrylamide (pNIPAm), capable, in first place, of housing cells up to confluence and, secondly, allowing the detachment of cells or cell monolayers by a thermal stimulus (lowering of temperature) has emerged as a potentially viable approach in cellular manipulation. This type of thermosensitive substrates are currently marketed (UpCell™). Once cell growth has reached the desired level of confluence, a monolayer or cell sheet can be detached simply by a decrease in temperature at room temperature (i.e., lower critical solution temperature, LCST). This approach of cellular detachment is a non-destructive and more moderate form of cellular collection than traditional methods, which require almost necessarily the use of aggressive proteolytic enzymes (usually trypsin) or cell scraping.

These techniques can damage the collected cells since they can cause disruption of the cell membrane and destroy the extracellular matrix. This disruption constitutes a significant deficiency in these cellular disaggregation approaches and therefore more moderate alternative detachment methods are desirable.

Therefore, the development of other alternatives for said soft detachment of cells and cell sheets is still necessary. An alternative thermosensitive polymer to pNIPAm is polyvinylcaprolactam (pVCL), which is biocompatible and has an LCST similar to that of pNIPAm (also in a physiologically relevant temperature range). However, few useful supports have been described in pVCL-based cell collection. Lee et al. (*Acta Biomaterialia;* 2013; 9 (8): 7691-7698) described the preparation of pVCL-thin films (about 50 nm) on woven Nylon substrates, using vapor phase chemical deposition techniques, and obtained partial cell detachment. Yang et al. described another example (*Polymer Chemistry;* 2015; 6 (18): 3431-3442) in which they prepared VCL independent hydrogels with a zwitterionic methacrylate, which were able to detach cells by lowering temperature.

Hydrogel-type supports for cellular manipulation based on vinylpyrrolidone—VP—, a component analogous to VCL but not thermosensitive, have been recently described. Specifically, it has been described the preparation of a family of non-thermosensitive hydrogels derived from VP and with a double pseudo-networks structure (pseudo-DN, in reference to the English term double network) capable of housing cells until confluence and subsequently allowing a fast detachment or transplantation of the cell sheet by means of a simple mechanical stirring, without the need of superstrate (an extra sheet that is required as an intermediate support for transplanting cells in the commercial product) (*Journal of Materials Chemistry B;* 2014; 2 (24): 3839-3848). The term pseudo-double network refers to the structural tendency of these networks to form double networks (DNs), which are defined as interpenetrated networks (IPNs) constituted by two networks with high asymmetry in cross-linking density. The aforementioned hydrogels are constituted by VP and by different ionic methacrylates M: anionic (M-$SO_3^-$), cationic (M-$N^+$), sulfobetaine type zwitterion phosphorylcholine type zwitterion (M-$PO_3^-$—$N^+$), or pseudo-zwitterionic formulations (stoichiometric amounts of M-$SO_3^-$ y M-$N^+$). All these hydrogels were robust despite their high water content (about 90% water in the equilibrium state). It was found that all the ionic hydrogels were superior in adhesion and cell proliferation to the control without ionic component (without M), what is in accordance with the well-known antiadhesive and antifouling nature of PVP and other neutral and water-soluble polymers (PEO (ethylene polyoxide), etc.).

Surface chemical and topographic modifications of mechanically robust polymers can modulate their interaction with the environment while maintaining the mechanical properties of the block. This fact seems to be especially relevant in fields such as tribology or medicine, in which custom-tailored resistant properties with superficial (both chemical and topographic) properties are sought after. On the one hand, the functionalization of hydrophobic supports to provide them with hydrophilic surface characteristics is currently a requirement for certain biomedical applications.

On the other hand, wrinkled surfaces have found application in multiple areas such as their use as templates to create orderly surface formations, or in the manufacture of flexible electronic components, or in the design of surfaces with wettability and controlled adhesion/friction properties. In addition, it is important to point out that supporting said hydrogels in the form of coating on mechanically robust materials, such as Nylon or polycarbonate, can significantly improve the handling of the active hydrogel layer, since the hydrogel support can be stapled, sewn, fused, etc., and therefore can allow forming complex constructs. The hydrogel can even be dried and rehydrated, which is advantageous in terms of storage under clean conditions and delivery. Finally, these platforms may be of interest in fields that require cellular sheet engineering, such as tissue transplantation in burned or cornea areas, examples in which the tissue regeneration process can be improved.

BRIEF DESCRIPTION OF THE INVENTION

The expression "based on" is to be understood as "formed by" or "formed from", that is to say that the constituents of the product referred to, may not be in the initial state in which they were used to obtain said product.

The expression "type" or "of the type" is to be understood as "similar to", or to include a certain functional group, for example: "vinyl-lactam type" should be interpreted as including at least one lactam functional group, and includes any vinyl lactam.

The term "gradient" refers to "concentration gradient" and has the usual meaning: variation of the concentration of both the polymeric substrate and the hydrogel network in the interface.

The term interface has the usual meaning, as defined by the IUPAC: the non-homogeneous spatial region, intermediate, between two massive phases in contact, and where the properties are significantly different from, but related to, the properties of the massive phases.

The term "roughness" refers in this specification and in this technology to protuberances that are formed in a material that was originally flat (as in the case of polystyrene) and said protuberances are micrometric and do not form any structure.

The term "wrinkles" refers to what in common language is called wrinkles, and have peaks and valleys, confer a structure to the material and are greater than roughness. The wrinkles in this case are therefore patterns that have been observed on PC and on PMMA with alternating valleys and peaks simulating a wrinkle in the skin. While in the case of PS wrinkles are not formed but the substrate (which was originally flat) increases its roughness due to the hydrogel layer.

A first aspect of the present invention relates to a product comprising:
a) a polymeric substrate and
b) a hydrogel based on vinyl-lactam type monomers, without methacrylates or with ionic methacrylates, and at least two crosslinkers,
characterized in that there is an interface between the substrate and the hydrogel, an interface formed by a gradient of both the substrate and the hydrogel network, both forming a semi-interpenetrated network, The hydrogel forms a polymeric network, and for this reason this specification in some cases refers to the "hydrogel network".

Semi-interpenetrated network means that the hydrogel coats the polymeric substrate in a stable way through the formation of a hybrid layer between substrate and hydrogel, an interface in which both structures coexist forming an integrated structure in the form of a semi-interpenetrated network (semi-IPN). This semi-IPN network type interface comprises the polymeric network constituting the hydrogel and the macromolecular chains of the polymeric substrate, and is characterized by a molecular-scale penetration of said chains in said network.

Particular embodiments refer to a product comprising:
a) a polymeric substrate and
b) a hydrogel based on vinyl-lactam type monomers, without methacrylates, in which the vinyl-lactam is vinylcaprolactam, the polymeric substrate is nylon, and two cross-linkers which are ethylene glycol dimethacrylate (C1) and 3,3'-(propyl)-di-1-vinyl-2-pyrrolidone (C2),
o
a) a polymeric substrate and
b) a hydrogel based on vinyl-lactam type monomers, with ionic methacrylates, and at least two crosslinkers,
characterized because there is an interface between the substrate and the hydrogel, interface formed by a gradient of both the substrate and the hydrogel network—both forming a semi-interpenetrated network structure.

The polymeric substrate can be any thermoplastic polymer substrate.

In a preferred example, the polymeric substrate is selected from polystyrene (PS), polymethyl methacrylate (PMMA), nylon, polycarbonate (PC), PVC (polyvinyl chloride), polylactic acide (PLA) or polycaprolactone (PCL). In a more preferred example, the polymeric substrate is nylon, polystyrene or polycarbonate. In an even more preferred example, the polymeric substrate is polystyrene.

In another particular example, the vinyl lactam is selected from vinylcaprolactam or vinylpyrrolidone. In a more preferred example, the vinyl-lactam is vinylcaprolactam.

In a particular example, the vinyl-lactam/ionic methacrylate molar ratio is in the range 2/1 to 100/1. In a more preferred example the ratio is in the range 6/1 to 12/1.

In a particular example, the ionic methacrylate is a cationic methacrylate selected from [2-(methacryloyloxy)alkyl]trimethylammonium salts, dimethylaminoethyl methacrylates and diethylaminoethyl methacrylates.

In another particular example, the ionic methacrylate is a zwitterionic methacrylate selected from methacryloyloxyethyl phosphorylcholine or [3-(methacryloylamino)propyl] dimethyl(3-sulfopropyl) ammonium hydroxide.

In another particular example, the ionic methacrylate is an anionic methacrylate selected from sulfoalkyl methacrylates salts.

In another particular example, the ionic methacrylate is a mixture of anionic methacrylate selected from sulfoalkyl methacrylates salts (for example, sulfopropyl methacrylate potassium salt) and of cationic methacrylate selected from [2-(methacryloyloxy)alkyl]trimethylammonium salts.

In a preferred example, the crosslinkers are selected from ethylene glycol di(meth)acrylate, triethylene glycol di(meth)acrylate, tetraethylene glycol di(meth)acrylate, trimethylolpropane tri(meth)acrylate, bisphenol A di(meth)acrylate, ethoxylate bisphenol A di(meth)acrylate, pentaerythritol tri-, and tetra(meth)acrylate, tetramethylene di(meth)acrylate, methylenebisacrylamide, methacryloxyethyl vinyl carbonate, triallylcyanurate, methacryloxyethyl vinyl urea, divinyl benzene, diallyl itaconate, allyl methacrylate, diallyl phthalate, polysiloxanylbisalkyl (met)acrylate, polyethylene glycol di(meth)acrylate, vinyl-methacrylate, divinyl-adipate, divinylpyrrolidone derivatives, 1,3-divinylimidazolin-2-one or combinations of thereof.

In a more preferred example, the crosslinkers used are: ethylene glycol di(meth)acrylate and 3,3'-(propyl)-di-1-vinyl-2-pyrrolidone.

In a preferred example, concentrations of each of the crosslinkers are used in the molar range 0.1-10% (with respect to moles of total monomers).

In an even more preferred example, total concentrations of the crosslinkers are used in the molar range 1.6-2% (with respect to moles of total monomers).

Another aspect of the invention relates to a method for obtaining the product described hereinabove, wherein the method comprises at least the following steps:
a) mixing the hydrogel precursor monomers, the vinyl lactam derivative, the ionic methacrylate, if present, and at least two crosslinkers with a photoinitiator and, optionally, solvent,
b) depositing the mixture of (a) on the surface of the polymeric substrate and induction of the photopolymerization under UV radiation
c) swelling of the product obtained in (b) by immersion in water or ethanol.

The solvent may be water, organic solvents such as alcohols, water and alcohols mixtures. Among the alcohols, for example, methanol, ethanol, propanol, or mixtures may be used. According to particular embodiments, the solvent is water.

In a preferred example, the polymeric substrate is selected from polystyrene (PS), poly(methyl methacrylate) (PMMA), nylon, polycarbonate (PC), PVC poly(vinylchloride), polylactic acid (PLA) or polycaprolactone (PCL). In a more preferred example, the polymeric substrate is nylon, polystyrene or polycarbonate.

In another preferred example, the vinyl-lactam is selected from vinylcaprolactam or vinylpyrrolidone. In a more preferred example, the vinyl-lactam is vinylcaprolactam.

In a particular example, the ionic methacrylate is a cationic methacrylate selected from [2-(methacryloyloxy)alkyl]trimethylammonium salts.

In another particular example, the ionic methacrylate is a zwitterionic methacrylate selected from methacryloyloxyethyl phosphorylcholine, [3-(methacryloylamino)propyl]dimethyl (3-sulfopropyl)ammonium hydroxide.

In another particular example, the ionic methacrylate is an anionic methacrylate selected from sulfoalkyl methacrylates salts.

In another particular example, the ionic methacrylate is a mixture of anionic methacrylate selected from sulfoalkyl methacrylates salts and cationic methacrylate selected from of [2-(methacryloyloxy)alkyl]trimethylammonium salts.

In a preferred example, the crosslinkers are selected from ethylene glycol di(meth)acrylate, triethylene glycol di(meth)acrylate, tetraethylene glycol di(meth)acrylate, trimethylolpropane tri(meth)acrylate, bisphenol A di(meth)acrylate, ethoxylate bisphenol A di(meth)acrylate, pentaerythritol tri-, and tetra(meth)acrylate, tetramethylene di(meth)acrylate, methylenebisacrylamide, methacryloxyethyl vinyl carbonate, triallylcyanurate, methacryloxyethyl vinyl urea, divinyl benzene, diallyl itaconate, allyl methacrylate, diallyl phthalate, polysiloxanylbisalkyl(met)acrylate, polyethylene glycol di(meth)acrylate, vinyl methacrylate, divinyl adipate, divinylpyrrolidone derivatives, 1,3-divinylimidazolin-2-one or combinations thereof.

In one example, crosslinkers used are, for example ethylene glycol di(meth)acrylate and 3,3'-(propyl)-di-1-vinyl-2-pyrrolidone.

In another particular example, UV radiation is maintained between 0.1 and 60 minutes. In a preferred example the radiation is maintained between 10 and 60 minutes, and in a more preferred example, the UV radiation is maintained for 40 minutes.

According to particular embodiments, the present invention refers to a product comprising:
a) a polymeric substrate selected from polystyrene, poly(methyl methacrylate), nylon, polycarbonate, poly(vinylchloride), polylactic acid or polycaprolactone and
b) a hydrogel based on vinyl-lactam type monomers, without methacrylates, or with ionic methacrylates and two crosslinking agents,
wherein there is an interface between the substrate and the hydrogel, an interface formed by a gradient of both, the substrate and the hydrogel network—both forming a semi-interpenetrated network—.

According to further particular embodiments the present invention refers to a product comprising:
a) a polymeric substrate and
b) a hydrogel based on:
vinylcaprolactam or vinylpyrrolidone monomers, without methacrylates, or
vinylcaprolactam or vinylpyrrolidone monomers with ionic methacrylates and at least two crosslinkers,
in which there is an interface between the substrate and the hydrogel, an interface formed by a gradient of both, the substrate and the hydrogel network—both forming a semi-interpenetrated network—.

According to further particular embodiments the present invention refers to a product comprising:
a) a polymeric substrate selected from polystyrene, polymethyl methacrylate, nylon, polycarbonate, poly(vinylchloride), polylactic acid or polycaprolactone and
b) a hydrogel based on vinyl lactam type monomers, ionic methacrylates selected from:
a cationic methacrylate selected from [2-(methacryloyloxy)alkyl]trimethylammonium salts, dimethylaminoethyl and diethylaminoethyl methacrylates,
a zwitterionic methacrylate selected from methacryloyloxyethyl phosphorylcholine, [3-(methacryloylamino)propyl]dimethyl(3-sulfopropyl)ammonium hydroxide methacrylate,
an anionic methacrylate selected from sulfoalkyl methacrylates salts, and
a mixture of anionic methacrylate selected from sulfoalkyl methacrylates salts and cationic methacrylate salts selected from [2-(methacryloyloxy)alkyl]trimethylammonium salts,
and at least two crosslinkers,
wherein there is an interface between the substrate and the hydrogel, an interface formed by a gradient of both, the substrate and the hydrogel network—both forming a semi-interpenetrated network—.

According to further particular embodiments the present invention refers to a product comprising:
a) a polymeric substrate selected from polystyrene, polymethyl methacrylate, nylon, polycarbonate, poly(vinylchloride), polylactic acid or polycaprolactone and
b) a hydrogel based on vinyl-lactam type monomers, with ionic methacrylates selected from:
a cationic methacrylate selected from [2-(methacryloyloxy)alkyl]trimethylammonium salts, dimethylaminoethyl and diethylaminoethyl methacrylates,
a zwitterionic methacrylate selected from methacryloyloxyethyl phosphorylcholine, [3-(methacryloylamino)propyl]dimethyl(3-sulfopropyl)ammonium hydroxide methacrylate,
an anionic methacrylate selected from sulfoalkyl methacrylates salts, and
a mixture of anionic methacrylate selected from sulfoalkyl methacrylates salts and cationic methacrylate salts selected from [2-(methacryloyloxy)alkyl]trimethylammonium salts, and at least two crosslinkers which are ethylene glycol di(meth)acrylate and 3,3'-(propyl)-di-1-vinyl-2-pyrrolidone.
wherein there is an interface between the substrate and the hydrogel, an interface formed by a gradient of both, the substrate and the hydrogel network—both forming a semi-interpenetrated network—.

According to further particular embodiments the present invention refers to a product comprising:
a) a polymeric substrate selected from polycarbonate, or nylon and
b) a hydrogel based on vinipyrrolidone (VP) or vinylcaprolactam monomers, with ionic methacrylates selected from: sulfopropyl methacrylate potassium (M-SO$_3^-$), [2-(methacryloyloxy)ethyl] trimethylammonium chloride ((M-N$^+$), [3-(methacryloylamino) propyl]dimethyl(3-sulfopropyl)ammonium hydroxide 2-methacryloyloxyethyl phosphorylcholine (M-PO$_3^-$—N$^+$), or a mixture of M-SO$_3^-$ and M-N$^+$) and at least two crosslinkers which are ethylene glycol di(meth)acrylate and 3,3'-(propyl)-di-1-vinyl-2-pyrrolidone.

wherein there is an interface between the substrate and the hydrogel, an interface formed by a gradient of both the substrate and the hydrogel network—both forming a semi-interpenetrated network—.

According to further particular embodiments the present invention refers to a product comprising:
a) a polymer substrate selected from polystyrene and polylactic acid and
b) a hydrogel based on vinylpyrrolidone (VP) or vinylcaprolactam monomers, and
at least two crosslinkers that are ethylene glycol di(meth) acrylate and 3,3'-(propyl)-di-1-vinyl-2-pyrrolidone.

wherein there is an interface between the substrate and the hydrogel, an interface formed by a gradient of both the substrate and the hydrogel network—both forming a semi-interpenetrated network—.

According to further particular embodiments the present invention refers to a product comprising:
a) a polymeric substrate that is nylon and
b) a hydrogel based on vinylcaprolactam monomers (VCL) and two crosslinkers which are ethylene glycol dimethacrylate) and 3,3'-(propyl)-di-1-vinyl-2-pyrrolidone (C2), wherein there is an interface between the substrate and the hydrogel, an interface formed by a gradient of both the substrate and the hydrogel network—both forming a semi-interpenetrated network—.

According to further particular embodiments the present invention refers to a product comprising:
a) a polymeric substrate that is polycarbonate and
b) a hydrogel based on vinylpyrrolidone (VP) monomers, with sulfopropyl methacrylate potassium (M-SO$_3^-$) and two crosslinkers that are ethylene glycol di(meth)acrylate and 3,3'-(propyl)-di-1-vinyl-2-pyrrolidone.

wherein there is an interface between the substrate and the hydrogel, an interface formed by a gradient of both the substrate and the hydrogel network—both forming a semi-interpenetrated network—.

Another aspect of the invention refers to the use of the material described above to obtain materials for cell culture.

Another aspect of the invention refers to the use of the material described above for the coating of 3D objects. Preferably, it refers to the use of the material described above for the coating of 3D objects for the manufacture of scaffolds.

Another aspect of the invention refers to the use of the material described above for the manufacture of thermosensitive mechanical actuators.

Another aspect of the invention refers to a method for obtaining materials for cell culture comprising depositing cells on a support constituted by the product of the present invention, and making them grow on the entire product surface.

Another aspect of the invention refers to a method for coating 3D objects comprising preparing a hydrogel on the surface of a 3D object. Preferably, the method is suitable for the coating of 3D objects for the manufacture of scaffolds.

Another aspect of the invention refers to a method for the manufacture of thermosensitive mechanical actuators comprising coating a flexible substrate with a heat-sensitive coating.

Unless otherwise stated, all technical and scientific terms used herein have the same meaning as commonly understood by skilled person in the field to which this invention belongs. Similar or equivalent methods and materials to those described herein, may be used in practice in the present invention. Throughout the description and claims, the word "comprise" and its variations are not intended to exclude other technical characteristics, additives, components or steps. Objects, advantages and additional features of the invention will become evident to the technical experts after examination of the description or can be learned through the practice of the invention. The following examples and illustrations are provided by way of illustration and are not intended to be limitative of the present invention.

DETAILED DESCRIPTION OF THE INVENTION

Examples

"Mold" is called in these examples the set of polymeric substrate+spacer+transparent lid.

1. Coating of Flat Nylon Substrates with VCL-Based Hydrogels and Ionic Methacrylates Hydrogels were synthesized by conventional radical polymerization in a single step using Milli-Q water, alcohols (ethanol or methanol) or water/alcohol mixtures as solvents. The polymerizable mixture consisted of a solution of vinylcaprolactam (VCL) (in the range 3-9 mol/L, in this example 6 mol/L), an ionic methacrylate (in the range 0.5-1 mol/L, in this example 1 or 0.5 mol/l) selected from: sulfopropyl methacrylate potassium (M-$SO_3^-$), [2-(methacryloyloxy)ethyl]trimethylammonium chloride ((M-$N^+$), [3-(methacryloylamino)propyl]dimethyl(3-sulfopropyl)ammonium hydroxide (M-$N^+$—$SO_3^-$), 2-methacryloyloxyethyl phosphorylcholine (M-$PO_3^-$—$N^+$), or a mixture M-$SO_3^-$ y M-$N^+$), the crosslinking agent ethylene glycol dimethacrylate (C1, in the molar range 0.5-4% versus the total monomer content) and the crosslinker 3,3'-(propyl)-di-1-vinyl-2-pyrrolidone (C2, 0.1 mol % versus total monomer content). Hydroxy-cyclohexyl phenyl ketone (HCPK) was used as a photoinitiator (0.5% by weight based on the total weight of monomers, in this example 2% of C1 and 0.1 mol % of C2 versus the total monomer content).

The formulas of the aforementioned methacrylates are shown below:

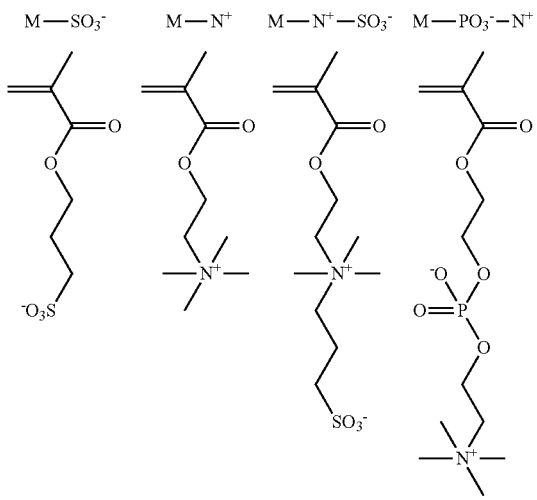

Figure 1:
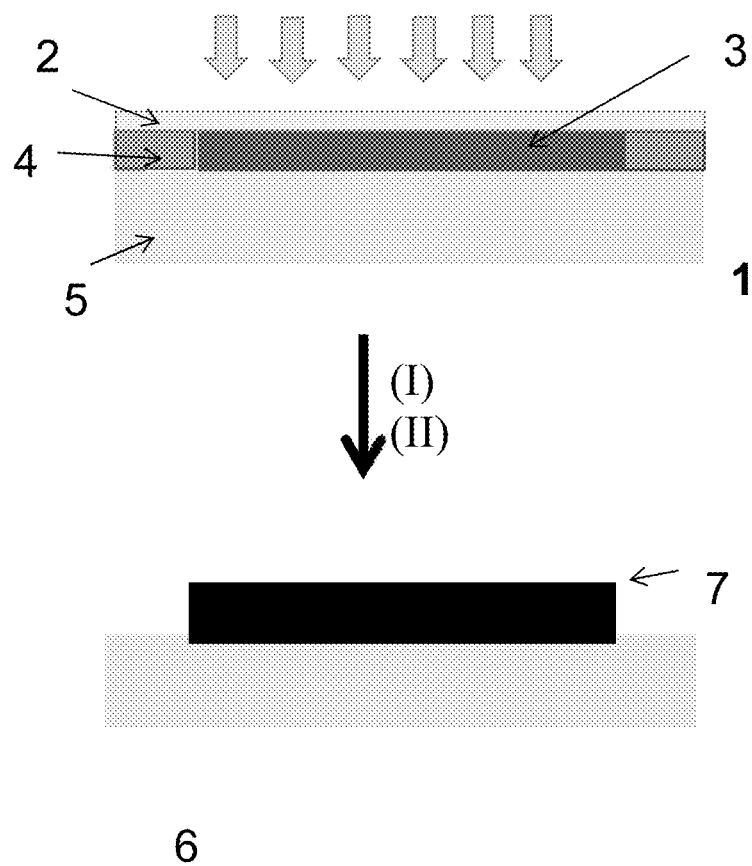
FIG. 1. Scheme of the mold used to prepare the product, in which the references mean:
1 Mold
2 Lid
3 Mixture
4 Spacer
5 Substrate
6 Substrate covered with hydrogel
7 Hydrogel FIG. 2. The photographs indicate the optical changes associated with the VPTT (volume phase transition temperature). At temperatures above the VPTT (left image), the polymer network is collapsed and looks white. Upon cooling first to the VPTT (central image) and later to temperatures below the VPTT (right image) the white color disappeared and a transparent coating was observed which indicates a solvation of the polymeric network.

The reaction mixtures were bubbled with $N_2$ and transferred to molds (see FIG. 1) by means of a syringe. For the preparation of hydrogel coated substrates, the mold was constructed with a lower sheet of the chosen polymeric substrate (Nylon in this example) and a top sheet of another transparent substrate (polypropylene-PP, polyethylene-PE, etc; PP was used in this example) separated by a 0.05 to 1.5 mm thick spacer (0.05 mm adhesive tape, 0.1 mm acetate sheets and 0.5 mm thick silicone membranes were used in this example). Photopolymerization was carried out for 40 minutes under UV radiation ($\lambda$=365 nm) in a UVP ultraviolet lamp (model CL-1000L, 230V). Hydrogel coated substrates were recovered from the molds by removing the transparent lids and allowed to swell in Milli-Q water until equilibrium was reached (24 hours). Subsequently, they were thoroughly washed with water to remove any soluble material.

2. Coating of Flat Nylon Substrates with VCL-Based and M-Free Hydrogels. Its Use as Support for Cell Culture The hydrogel prepared using VCL, as well as ethylene glycol dimethacrylate (C1) and 3,3'-(propyl)-di-1-vinyl-2-pyrrolidone (C2) as crosslinkers (this is, without M), was prepared as in Example 1, except that M was not added and it was chosen to carry out preliminary cell culture studies.

Figure 2:
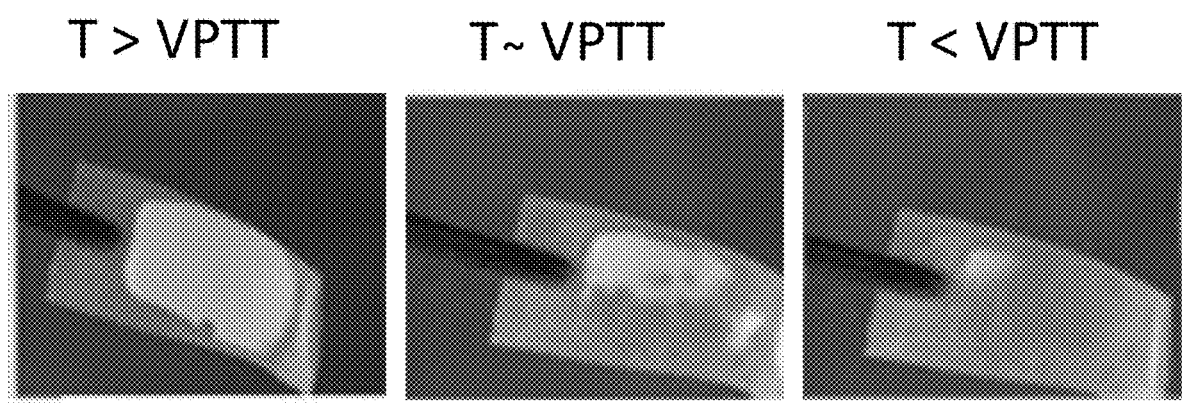

Photopolymerization of the VCL-based formulation on this material (Nylon) produced a hydrogel with an interface integrated on the surface of the coating support, produced a thereto-sensitive hydrogel coating as shown in FIG. 2. This hydrogel was stable and did not separate or break by manipulation or temperature changes when submerged in aqueous medium. Moreover, the hydrogel layer can be perfectly dried and rehydrated.

Figure 3:
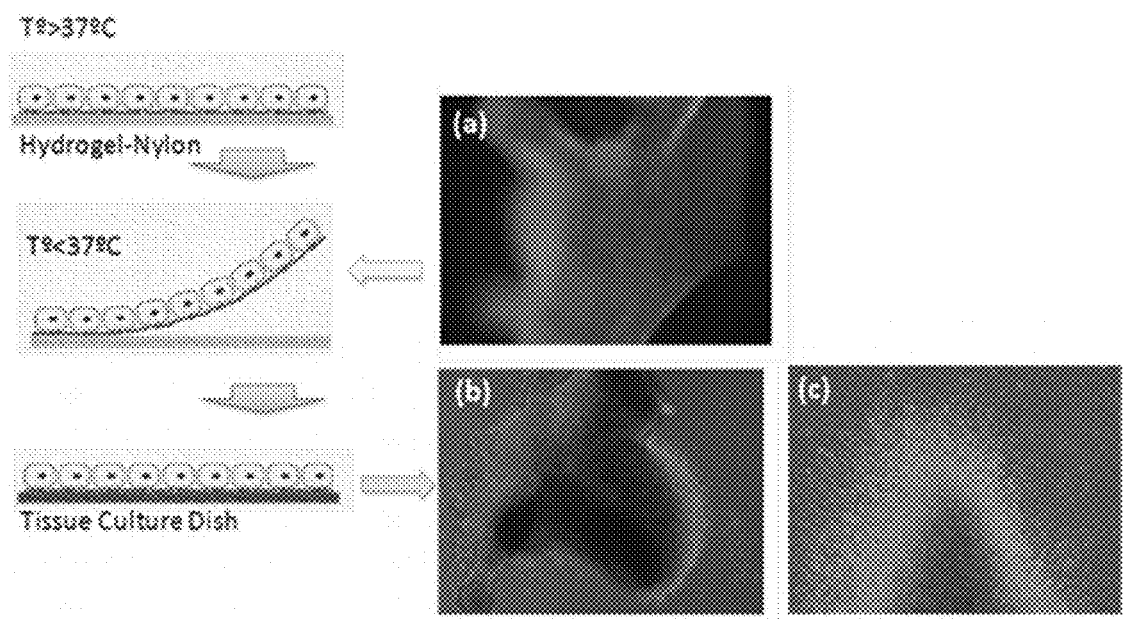
FIG. 3. Evaluation of monolayer formation in nylon coated with hydrogel. Upon cooling from 37 to 20° C. (below VPTT) the monolayer is separated (a) and the cells are transplanted onto a culture dish. As evidenced at 44 h (b) and 144 h (c), a complete monolayer can be formed from the transplanted cells.

This coated Nylon was evaluated as cell culture support using C166-GFP endothelial cells (FIG. 3). A cell monolayer was formed after a few days and this monolayer could be completely separated by decreasing the temperature (FIG. 3 (a)). After the transplant of the monolayer recovered on a culture plate, the cells were able to grow and to form again a monolayer after a few days.

All hydrogels were sterilized with 70% ethanol solution by rinsing six times for 10 minutes each. Next, they were washed with PBS six times, exposed to UV radiation for 30 minutes on each side of the hydrogel and washed twice with Dulbecco's modified Eagle's medium (DMEM) with high glucose content. To simulate the temperature of the culture conditions (37° C.), temperature that is above the transition temperature, a hot plate with a constant temperature was used for the material cutting process, obtaining samples of 2 cm$^2$ that fit in the 24-well plates. After cutting, the samples were incubated overnight with DMEM 10% fetal bovine serum (FBS) and 1% antibiotics (100 U/ml penicillin and 100 µg/ml streptomycin sulfate, Sigma-Aldrich, St Louis, Mo.).

C166-GFP (ATCC® CRL-2583™) is a mouse endothelial cell line transfected with green fluorescent protein (GFP). The culture conditions are Dulbecco's MEM (D6429) supplemented with 10% FBS plus 100 U/mL penicillin and 100/ml streptomycin sulfate adding 0.2 mg/ml of antibiotic G-418 to the culture medium for selection of GFP retained cells. The cells were seeded in the networks with a 3×10$^4$ cells/ml density and incubated at 37° C. with 5% $CO_2$. The cells were monitored using an inverted fluorescence microscope with a FITC filter ($\lambda_{ex}/\lambda_{em}$ 488/568 nm).

The hydrogels supporting the cell cultures were turned over and placed in new TCP wells. Subsequently, cold medium was added to each well to reach T≤27° C. A temperature probe was used to monitor this process. After 45 minutes, the hydrogels were removed and samples were re-incubated at 37° C. with $CO_2$. The transplanted cells were daily observed using an inverted fluorescence microscope and micrographs were taken. The Trypan Blue assay was performed following manufacturer's instructions.

The metabolic activity of the cellular transplants was measured by Alamar Blue assay following manufacturer's instructions. This method is non-toxic, scalable and uses the natural reducing power of living cells, generating a quantitative measure of cell viability and cytotoxicity. Briefly, Alamar Blue dye (10% of the culture volume) was added to each well, which contained live cells seeded on films, and incubated for 90 minutes. The tests were carried out, in each type of sample, in triplicate. The fluorescence ($\lambda_{ex}/\lambda_{em}$ 535/590 nm) of each well was measured using a plate-reader.

3. Coating of Polycarbonate Flat Substrates with VP-Based Hydrogels and Ionic Methacrylates As a starting point in all cases, a previously optimized VP-based formulation was used: water as a solvent, VP and M-$SO_3$ in concentrations of 6 and 1 mol/L respectively, two crosslinkers (denominated C2 and C1) with molar percentages (with respect to the monomers) of 2.0 and 0.1 respectively. Hydrogels were synthesized as described hereinabove. A summary of the hydrogel types prepared are given in Table 1.

TABLE 1

Photosensitive precursor solutions employed comprising: 6 mol of VP (1.265 ml), 2 mol of M—$SO_3$ (492 mg), 0.1 mol % of C2 (3.1 mg), and different amounts of both C1 and solvents (mixture of water and ethanol). The contact times used prior to the photopolymerization were 0, 5, 10, 20 and 30 minutes.

| Name | | HYD_1 | HYD_2 | HYD_3 | HYD_4 | HYD_5 | HYD_6 | HYD_7 |
|---|---|---|---|---|---|---|---|---|
| C1 (mol %) | | 2.0 | 2.0 | 2.0 | 2.0 | 0.5 | 1.0 | 4.0 |
| Solvent | EtOH | — | — | 0.245 | 0.490 | — | — | — |
| (ml) | Water | 0.735 | 1.000 | 0.490 | 0.245 | 0.735 | 0.735 | 0.735 |

The polypropylene lids were removed after the photocuring, and the networks formed on the PC substrates were allowed to swell in ethanol until equilibrium was reached. Subsequently, the residual PC substrates were exhaustively washed with ethanol and water to remove any soluble material and finally they were dried for analysis.

In this example the compounds with wrinkles are formed, part of the hydrogel is detached when swelling and the wrinkles remain.

Cross sectional profiles and 3D images of the wrinkled surfaces were characterized by using a Zeta-20 True Color 3D Optical Profiler from Zeta Instruments. Static contact angles measurements were performed by using a contact angle goniometer (Tetha, KSV instruments) with the sessile drop method. In addition to the static contact angle values, advancing and receding contact angle values were carried out. A motorized syringe was set to a specific speed to control the volumetric flow rate of the liquid to, or from, the sessile drop. The mechanism pushed the syringe plunger during the advancing procedure and pulled it during the receding procedure, leading to an increase and decrease of the drop size, respectively. Images of the growing and shrinking drop were then recorded by the computer, typically at a rate of a picture every 1 s. In this study, the advancing and receding processes were repeated at least 7 times, taking the system through 7 cycles.

The chemical composition and depth profiles of the polymeric films were determined using Confocal Raman Microscopy integrated with atomic force microscopy (AFM) on a CRM-Alpha 300 RA microscope equipped with Nd:YAG dye laser (maximum power output of 50 mW power at 532 nm). The Raman spectra were taken point by point with a step of 100 nm.

The precursor formulation that has been labeled as HYD_1, is shown to be able to induce a superficial microstructure in PC surfaces, the latter was obtained in one single step by UV-initiated polymerization of the monomeric HYD_1 solution deposited on a PC substrate (using the setup depicted in FIG. 3), followed by separation of the hydrogel by swelling in ethanol.

The HYD_1 solution was confined between a transparent lid and the polycarbonate substrate using a spacer. The hydrogel, resulting after a lag time of 10 minutes and a UV-vis photopolymerization step, was submerged in an EtOH solution. Upon swelling, the hydrogel detaches from the PC support leaving a substrate in which the topography has been significantly modified. Illustrative 3D optical profile images of a non-treated PC surface and after the UV-photopolymerization step are depicted in FIG. 3. In contrast to the non-treated planar PC surface, the surface of the films obtained after hydrogel removal shows randomly distributed wrinkles. In particular, under the conditions described before, wrinkles with homogeneous dimensions (around ~30 mm in wavelength and amplitudes of around ~9 mm) over the entire surface were observed. This particular surface topography on the PC surface must be related to the hydrogel formation and post-polymerization detachment upon immersion in ethanol. It has to be noted that control experiments carried out without the small percentage of 0.1 mol % of the divinyl compound C2 did not render a homogeneous hydrogel swelling/detachment, neither wrinkles. C2 plays a key role not only for the network properties but also due to its possible participation in links between chains rich in SPM and chains rich in VP. Analogous heterolinks have been described to enhance mechanical properties of true DNs. Besides, an increase of C1 to 4 mol % leads to either a partial detachment or a complete anchoring of the hydrogel to the PC. This influence of C1 on the hydrogel detachment will be addressed later.

It is hypothesized here that the formation of the wrinkles of FIG. 3 is somehow related to a PC swelling and therefore to a penetration of the monomer mixture into the outer PC layers. The detachment of the hydrogel upon swelling in ethanol would reveal the wrinkles. To address this hypothesis, the influence on the superficial wrinkling of different parameters which may influence the proposed monomer diffusion into PC, such as solvent type or the exposure time between the substrate and the photopolymerizable solution prior to the UV-irradiation, have been studied. Besides, the surface chemical composition has been analyzed; first, the potential changes on the surface wettability were analyzed by advancing and receding contact angle measurements. Second, the potential changes on the chemical surface composition were investigated by using confocal Raman microspectroscopy.

Figure 4:
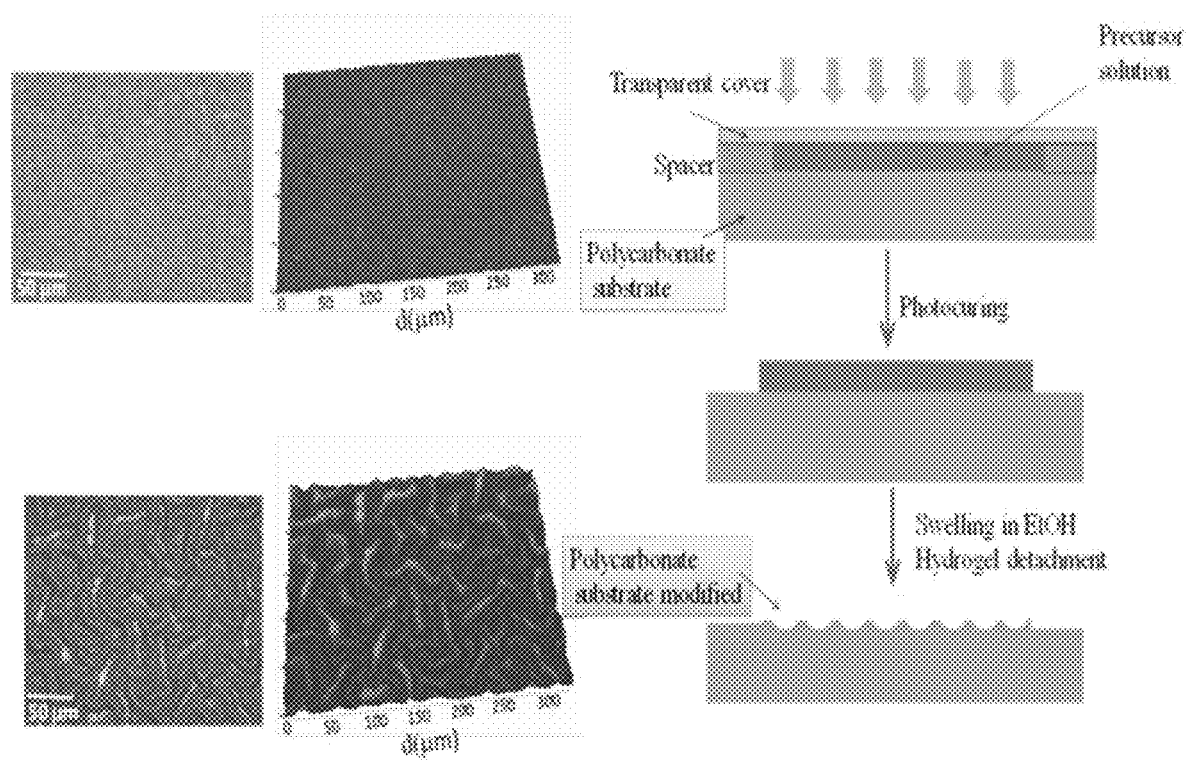
FIG. 4. Assembly for the manufacture of PC (polycarbonate) surfaces modified with VP-based hydrogels, together with optical profilometry images illustrating original PC films and a wrinkled PC surface obtained after the photopolymerization of a precursor solution (HYD_1) placed on the surface of the PC.

To analyze the influence of contact time, the monomer mixture HYD_1 was brought in contact with the PC surface and the lag time between the contact established and the initiation of the UV-light irradiation period was varied between 0 and 30 min (note that the sample depicted in FIG. 3 was obtained after a lag time of 10 minutes). As observed in FIG. 4, the superficial topography gradually varies from a rather planar substrate to a wrinkled surface by increasing the contact time. Short contact times produced only a slight increase of the superficial roughness (FIG. 4($a$)). However, the superficial topography significantly changes maintaining the precursor solution in contact with the substrate during 5 min or longer. In this situation (5 min), the surface resulting upon complete hydrogel detachment revealed the formation of wrinkles with periods around ~20 µm and amplitudes below 3 µm (FIG. 4 ($b$)). In the period of time observed, i.e. from 0 up to 30 minutes, a gradual increase of the wrinkle dimensions was observed. As a result, the wrinkles with periods ranging between 19 µm y 40 µm and amplitudes comprised between 2.6 µm y 17 µm could be easily prepared just by increasing the time elapsed between the contact of the precursor solution and the UV-vis photocuring step.

In addition to the contact time, the nature and ratio of the solvents employed for the photosensitive mixture may have a strong influence on the superficial swelling process of PC. HYD_1 used a small and optimized amount of water as solvent. To address this issue, samples HYD_2 to HYD_4 in Table 1 have been studied, were the amount and the nature of the solvent have been varied.

Figure 5:
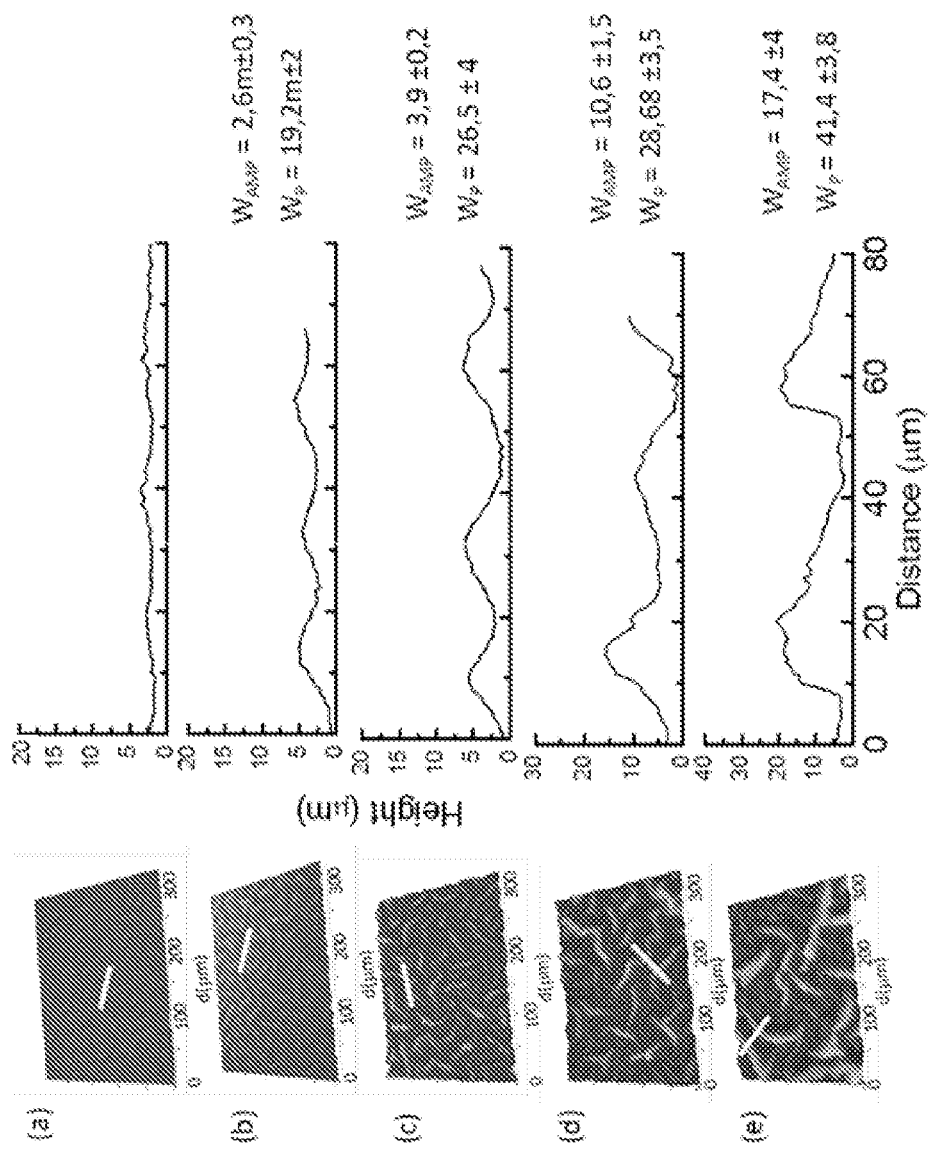
FIG. 5. Evolution of the superficial topography of PC that leads to the formation of wrinkles as a function of the time elapsed between the contact of the solution HYD_1 with the PC substrate and the beginning of the photopolymerization stage: (a) 0 min, (b) 5 min, (c) 10 min, (D) 20 min and (e) 30 min. W$_{AMP}$: wrinkles width, W$_p$: wrinkles period.

The wrinkle dimensions (amplitude and period) clearly varied depending on the solvent employed. The optical 3D profile images and two additional graphs representing the variation of the wrinkle characteristics as a function of the contact time for different precursor solutions are depicted in FIG. 5. By using the HYD_2 solution with a larger amount of water then in the case of HYD_1, the wrinkles observed are clearly smaller than those observed using HYD_1. On the other hand, partial substitution of water by EtOH leads to wrinkles with larger dimensions. Moreover, an increase in the amount of EtOH in the solvent mixture resulted in wrinkles with larger periods and amplitudes. Therefore, beyond water addition, the inclusion of a further solvent with higher affinity to the substrate allowed us to finely tune the resulting wrinkle dimensions. In particular, as depicted in FIG. 5, structured wrinkled surfaces, with periods between 10 and 100 µm and amplitudes ranging between 1-20 µm, were straightforwardly obtained.

Figure 6:
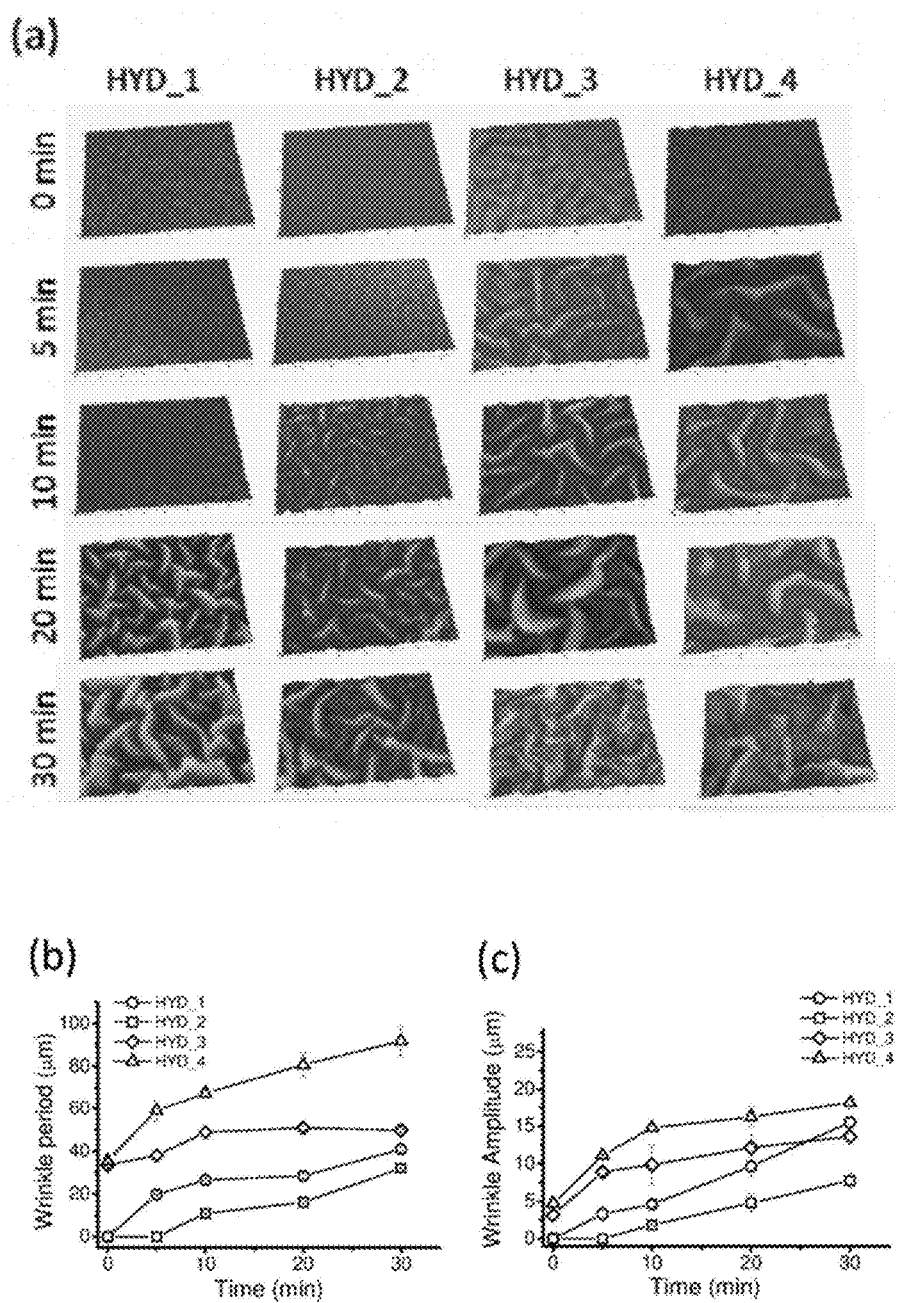
FIG. 6. (a) Morphological evolution of wrinkles depending on the solvent mixture used (Image size: 350 μm×250 μm). Variation of the period of the wrinkles (b) and its amplitude (c) as a function of the exposure time of the monomer solution to the PC substrate. HYD references are given in Table 1.

Regarding the chemical nature of the surface, static contact angle measurements carried out on both planar and non-modified and modified PC, indicated an increase of the superficial wettability, i.e. the treated surface becomes more hydrophilic (FIG. 6($a$)). A sample of HYD_1 type with 10 minutes contact time has been chosen for this study. Advancing and receding angle measurements evidenced significant surface changes. In FIG. 6($b$) the advancing and receding contact angles of 7 cycles observed for treated and untreated substrates are represented. The precursor substrate, i.e. pure PC, exhibits advancing angles of around 90-93° and receding contact angle values of 15-18°. These values remain constant during all the cycles explored. However, for the surfaces treated with the photosensitive mixture and upon hydrogel detachment, the advancing contact angle exhibits significant differences between the first and the following cycles. Whereas, in the first cycle, the advancing water contact angle exhibits values around 82° the values measured for the following cycles are around 10-12°. This interesting observation indicates that in the first cycle the treated interface requires a first wetting to become highly hydrophilic. Most probably, part of the hydrogel formed remains anchored at the interface hydrated during the following cycles. The advancing of the water front during the advancing angle measurements has been imaged by using an optical profiler (FIG. 6($c$)). The water droplet wets the valleys formed by the wrinkles and advances forming a thin water layer. Equally, as expected, the receding contact angle on the treated films is very low with values below 10°.

Contact angle experiments evidenced the formation of a hydrophilic superficial layer but they do not provide any information about the surface chemical composition and the depth profile of the treatment. Information about these two aspects was achieved by Raman Confocal. Prior to the investigation of the modified substrates, the differences between the Raman spectra of the PVP based hydrogel and the PC substrate were evaluated. By comparison of these two spectra we observed several characteristic signals. First, the signal found at 1675 cm$^{-1}$ corresponds to the C=O groups of the PVP-based hydrogel. However, the carbonyl functional groups present in the PC provide a Raman signal at 1613 cm$^{-1}$. In addition, the bands found at 1495, 1457, 1425 cm$^{-1}$ correspond to the main chain methylene deformation of the PVP material. Finally, the band at 944 cm$^{-1}$ is due to the pyrrolidone ring breathing mode and those observed at 860 and 768 cm$^{-1}$ due to the ring modes.

Figure 7:
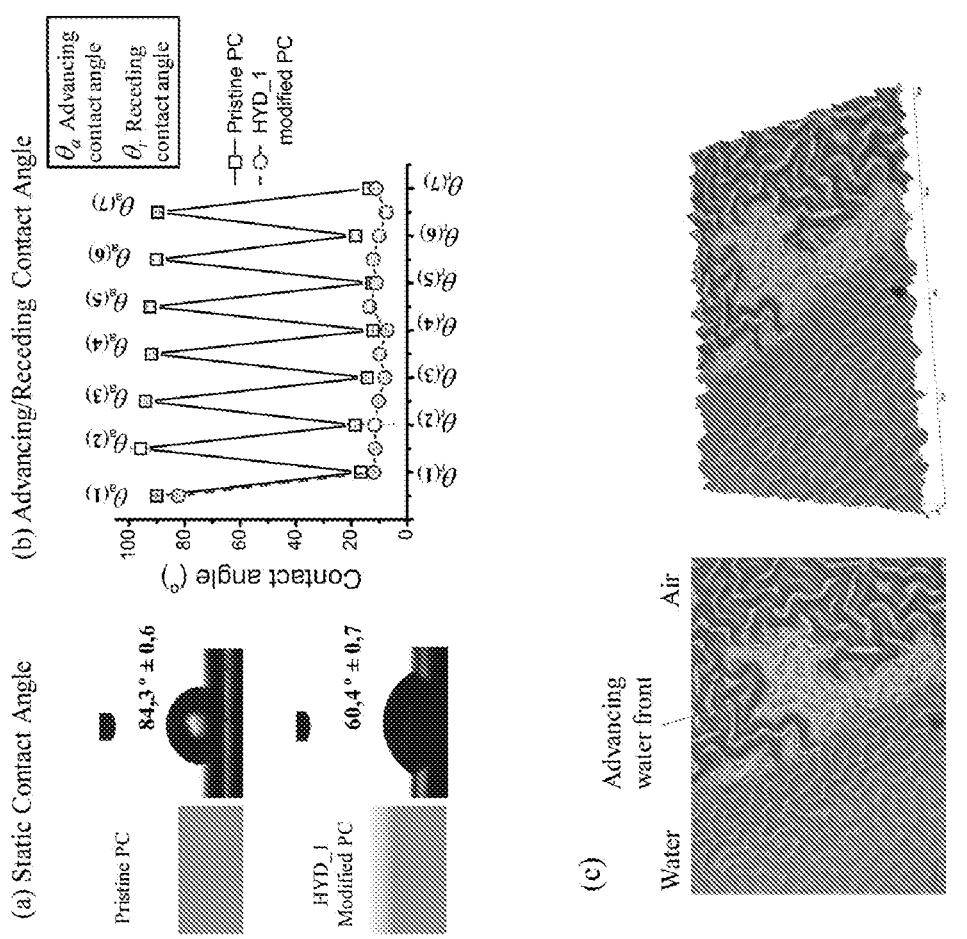
FIG. 7. (a) Measures of static contact angle and (b) forward-backward contact angle for 7 cycles in a treated and untreated PC. (C) Optical profilometry image of a water droplet advancing in the wet-dry interface. The surface of the wrinkled PC was obtained after the photopolymerization of a precursor solution HYD_1 placed on the surface of the PC with a time lapse of 10 minutes between contact and UV irradiation.

In the Raman spectrum observed for the treated PC substrate it can be clearly observed the formation of a top layer in which the chemical composition is a mixture of PC and VP based hydrogel. A further interesting feature of confocal Raman microspectroscopy is related to the possibility to obtain depth profiles that show the variation of the chemical composition from the surface to the interior of the PC. For this analysis the top of a wrinkle hill was employed as reference and Raman spectra were recorded at different depths up to 30 μm. The Raman spectra of HYD_1 obtained at different depths at different contact times, show a gradual variation of the spectra from a pure hydrogel mainly composed by PVP, to pure PC at a depth of 30 μm. By normalizing the signal at 1615 cm$^{-1}$ assigned to the C=O of PC, a gradual decrease can be easily observed following, for instance, the bands at 1495, 1457, 1425 cm$^{-1}$ due to the main chain methylene deformation or the band at 1678 cm$^{-1}$ due to the C=O groups of the hydrogel formed. As a result, a comparison of the bands at 1676 cm$^{-1}$ observed in the hydrogel and the band at 1615 cm$^{-1}$ characteristic of PC allows us to estimate the variation of the chemical composition and the depth of the modified layer. As depicted in FIG. 7, plotting the relation between both signals permits to construct cross-sectional profiles indicating the extent of the superficial modification. An increase of the contact time of the photopolymerizable solution on the substrate and the UV-vis irradiation step leads to an increase of the wrinkle dimensional characteristics.

As contact time increases, monomer mixture penetrate deeper into the PC, swelling occurs to a larger extent and surface instabilities appeared. Photopolymerization forms the VP-based network (actually the integrated hydrogel/PC outer layers form a semi-interpenetrated structure) and 'freezes' the superficial deformation. The detachment of the hydrogel, finally, reveals the wrinkles at the interface. According to the observations described above using the 3D optical profiler, the wrinkle size increases as the modified layer increases as well. Therefore, the process of wrinkle formation is directly related to the extent of swelling.

FIG. 7 also shows the relevance of the monomer concentration by comparing HYD_1 with HYD_2. While HYD_1 is prepared using 0.735 ml of water, HYD_2 containing 1 ml of water, is less concentrated. First of all, as depicted in the cross-sectional profiles and summarized in the graphs (FIGS. 7 (k) and (l)), the profiles indicate a larger diffusion of the hydrogel precursor components by increasing the monomer concentration. Whereas, HYD_2 exhibits monomer penetration profiles with thicknesses below 15 μm, HYD_1 evidenced that the superficial region affected is above 25 μm thick.

Figure 8:
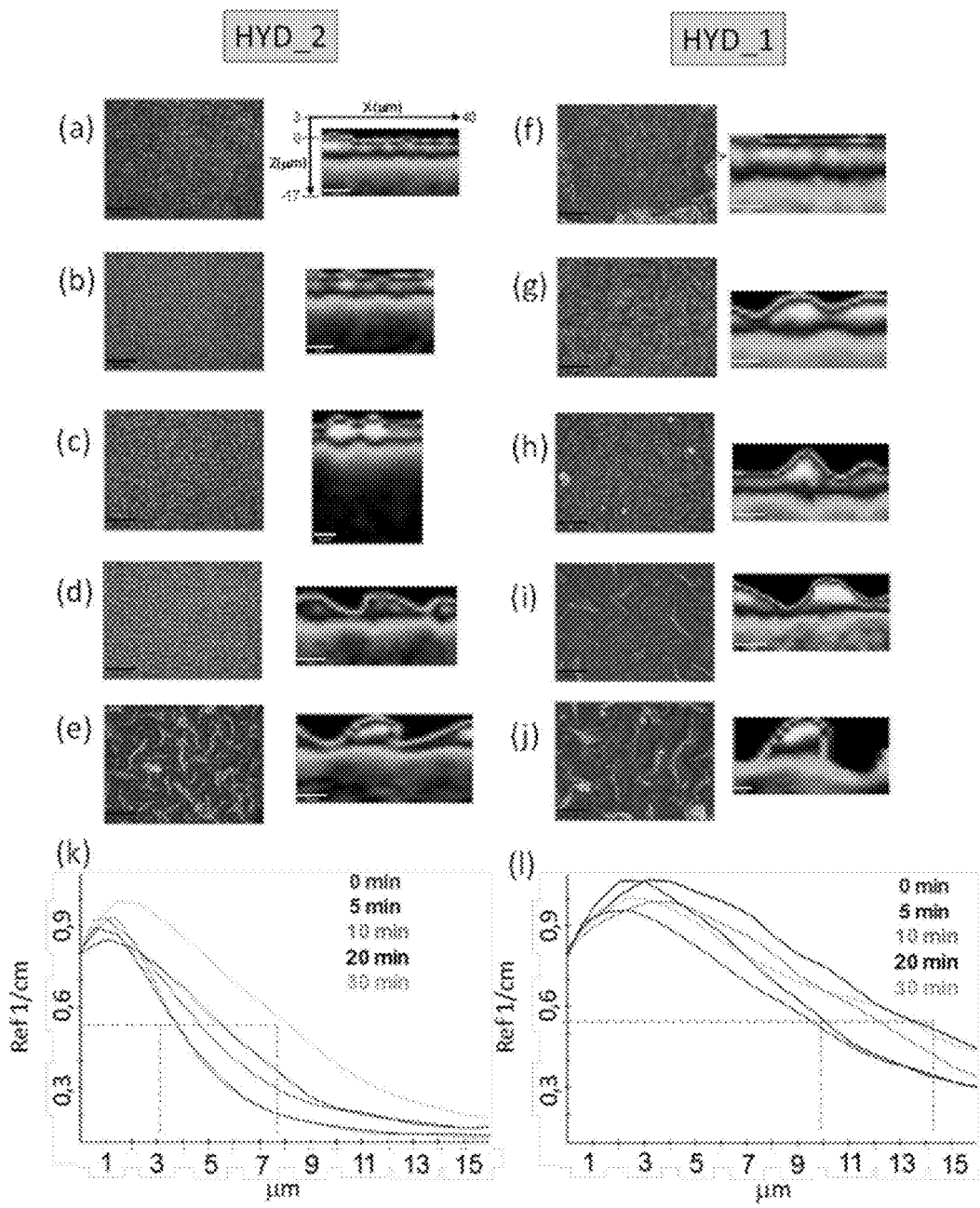
FIG. 8. Above: Representation of the ratio of intensities between the signals at 1676 cm$^{-1}$ observed in the hydrogel and the band at 1615 cm$^{-1}$ assigned to the PC as a function of the depth of HYD_2 (a-e) and HYD_1 (f-j). Below: Evolution of the Raman spectrum as a function of the depth of HYD_2 (k) and HYD_1 (l).
Figure 9:
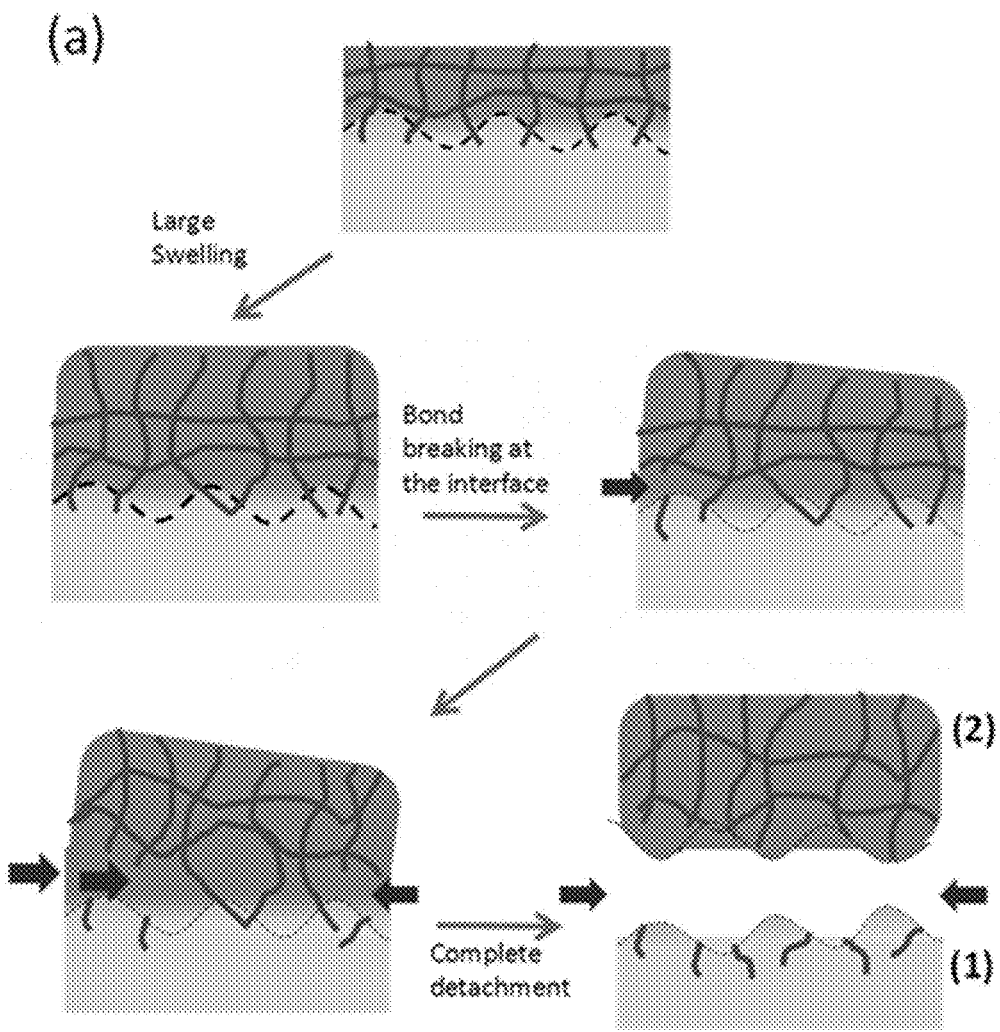
FIG. 9. Formation of VP-based hydrogels and situations observed after hydrogel swelling. Mainly two different possibilities were observed: (a) separation of the non-integrated regions of the hydrogels leaving a thin layer of hydrogel on top of the surface and (b) the hydrogels remain partially or completely anchored to the surface. (c) Optical images and illustrative 3D optical images of a PC surface after treatment (left) and the complementary hydrogel surface obtained on drying (right).
Figure 9:
Figure 9:
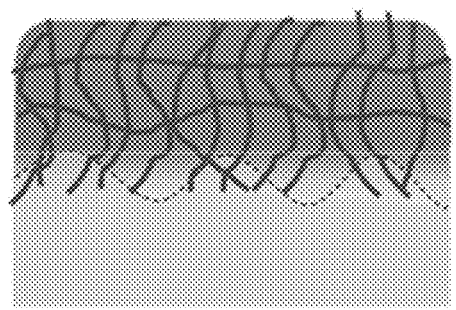
Figure 9:
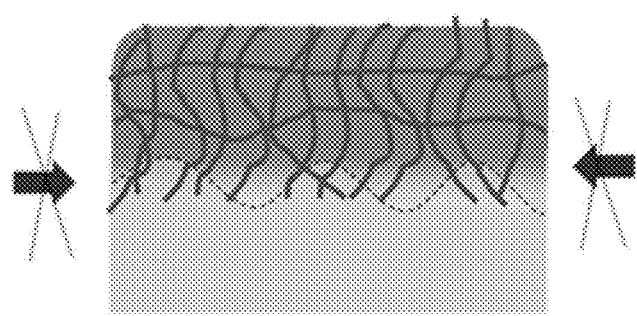
Figure 9:
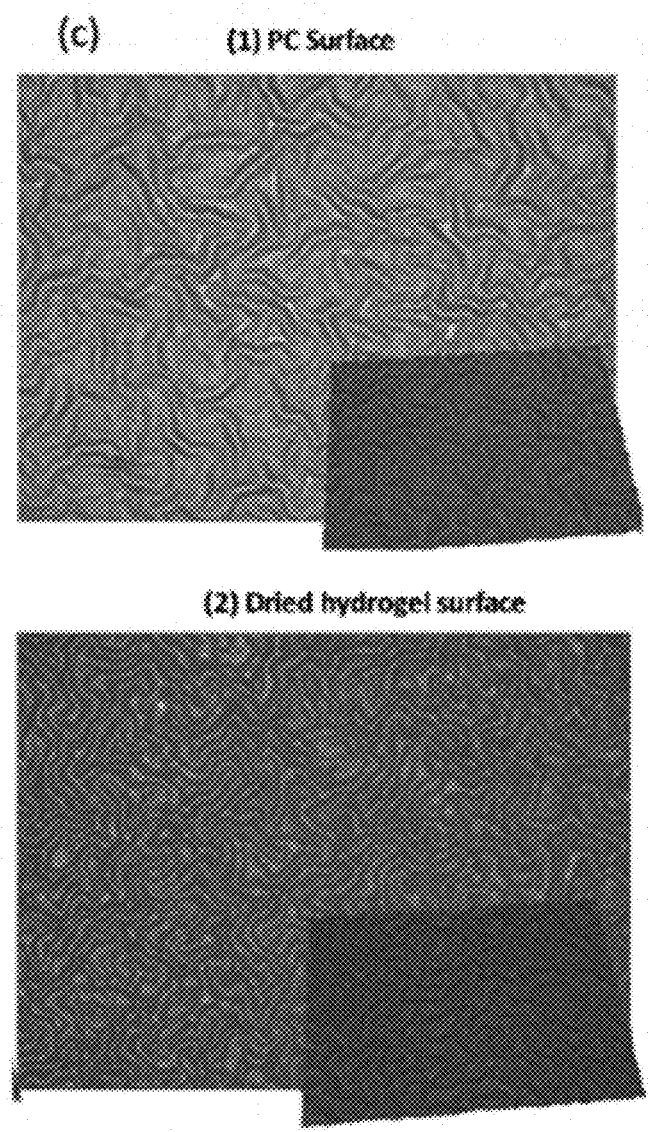

In the previous scenario of gradient swelling and surface deformation, the wrinkles become visible if the hydrogel is able to detach at the deformed interface. Based on related literature, hydrogel detachment may be related to the tensions originated at the surface upon hydrogel swelling and is influenced by the number of anchoring points established between the hydrogel and the PC substrate. This number of anchoring points is strongly related to the crosslinking degree. As it was mentioned before, an increase of C1 leads to either a partial detachment or a complete anchoring of the hydrogel to the PC substrate (depending on the contact time). A value of C1 between 0.5 and 1 mol % of crosslinking agent, resulted, however, in a complete detachment of the hydrogel from the PC leading to the wrinkling described herein. Interestingly, the surface of the hydrogel (FIG. 8(c)) also exhibits the formation of wrinkles which are complementary to the wrinkles observed in the PC surface. A hypothetic model has been developed according to these results (see FIG. 8). The networks of higher crosslinking density are able to absorb a limited amount of solvent and thus exhibit a reduced swelling and minor tensions related to the swelling phenomenon. The number of anchoring points between the interface and the hydrogel increases as well. Therefore, a critical crosslinking degree is proposed, below which there is a bond breaking at the interface and a hydrogel detachment. This is due to the reduced number of anchoring points and to the higher extension of tensions during swelling when compared to crosslinking degrees above the critical point, which are able to keep the full hydrogel anchored.

As a conclusion, it can be established that the selected mixture of monomer/crosslinking agents when in contact with PC diffuses and swells the polymer surface. As a result, upon swelling of the hydrogel formed either in EtOH or water, a controlled hydrogel detachment takes place, leaving a thin hydrogel layer at the PC surface. This thin layer of hydrogel is a consequence of the initial process of diffusion and swelling of the PC surface by the hydrogel precursors. The observed diffusion has two simultaneous consequences. First, the superficial chemical composition of the CP is altered and a surface with greater hydrophilicity is obtained. Secondly, the diffusion and swelling of the surface of the PC induces superficial instabilities that finally give rise to the formation of wrinkled surfaces. Interestingly, by modifying the composition of the precursor solution, as well as the contact time, a reasonable control over the characteristics of wrinkles (period and amplitude) is obtained.

Use in Cell Cultures

These supports are capable of allowing adhesion and proliferation of C166-GFP endothelial cells. It has been observed that cells can grow on the entire surface of the material, both within the wrinkles and in the most superficial part of the same. In addition, the proliferative activity of the culture on the support is greater than on the free VP hydrogel. Finally, it has been verified that the capacity of transplantation of the cell culture from these supports does not decrease with respect to the original VP hydrogel. In this way, cellular transplants have been obtained by inversion from the supports to new PS surfaces, totally viable and with a metabolic activity similar to that obtained with VP hydrogels.

Figure 10:
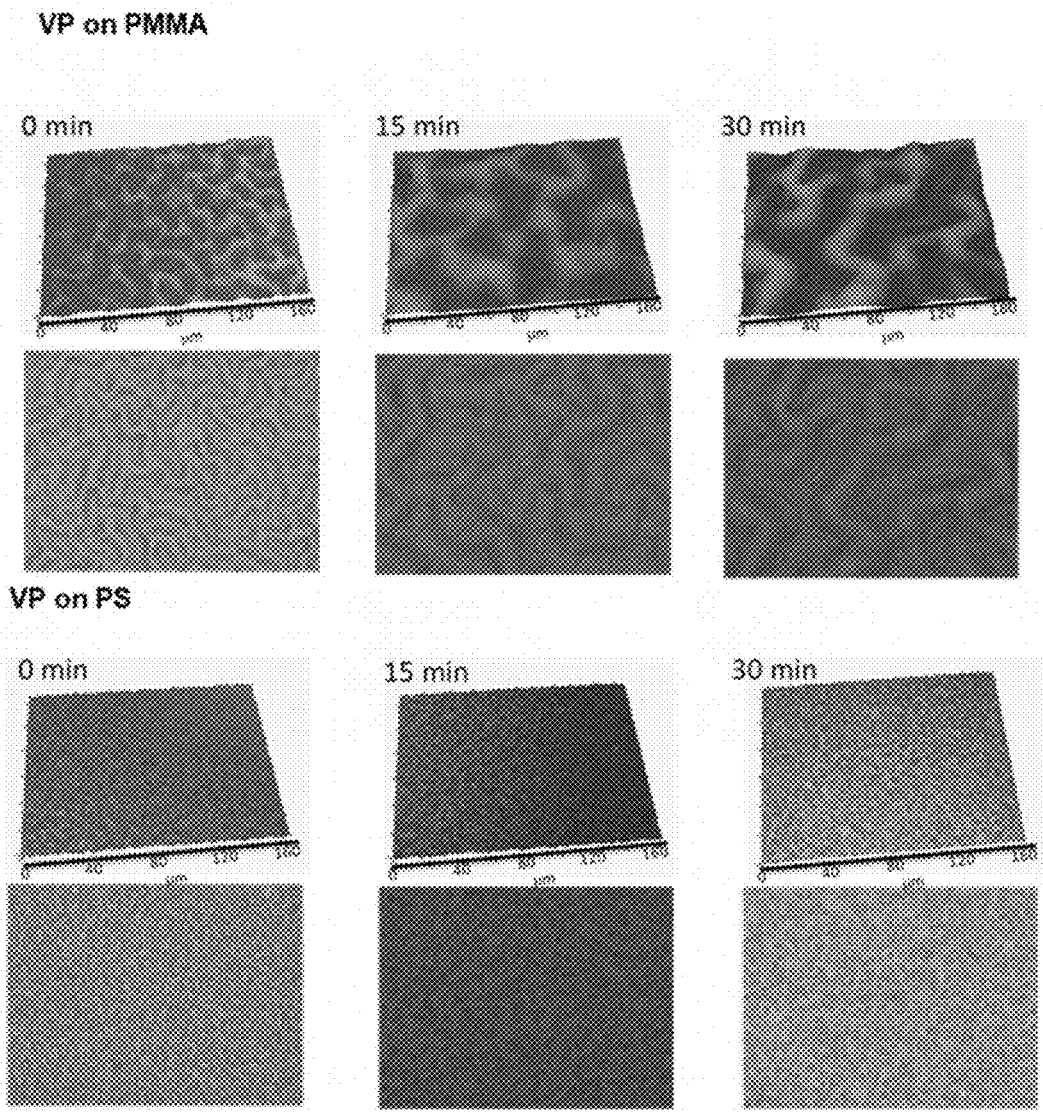
FIG. 10. Cell growth on surfaces based on PPMA substrates coated with VP-based hydrogels (with 0, 15 and 30 minute treatments). In the first line, the growth of the C166-GFP cell culture can be observed 72 h after sowing. In the second line, cellular transplants performed by reversing the material on plastic treated for cell culture at 24 h post-transplant. In the third line, cultures in confluence at 168 h post transplant.

4. Coating of Flat Substrates of Polymethyl Methacrylate (PMMA) and Polystyrene (PS) with VP Based Hydrogels and Anionic Methacrylate The hydrogel was prepared as in example 3, except that PMMA or PS was used instead of PC as a substrate, and only coatings with the sulfopropylmethacrylate potassium salt as a comonomer were made as a demonstration. As in Example 3, coatings were prepared using different residence times of the formulation (0, 15 and 30 minutes) (FIG. 10). With these substrates again, a detachment of the hydrogel layer was observed which is not part of the interface, although in this case the surface does not form wrinkles but forms roughness.

These coatings were studied as supports in cell culture following the protocol indicated in example 2. For the PMMA coatings (FIG. 11), after seeding with autofluorescent C166-GFP endothelial cells, it was possible to verify that all the evaluated surfaces are biocompatible (they allow adhesion and proliferation). The topography of the surface, which includes grooves and roughness, favors adhesion with respect to the original vinylpyrrolidone hydrogel (VP). Due to its composition, it had been described that cell growth occurred in the form of clusters. In materials based on PV coatings on PMMA this behavior persists for all treatments (there are almost no differences between 0, 15 and 30). However, it can be observed that the cells at the base of the clusters adhere preferentially to the grooves of the microstructure. The cells proliferate correctly over time, being possible to highlight some improvement over the original VP hydrogel.

It has been described that the original VP hydrogels allow the spontaneous detachment of cellular monolayers by mechanical stirring or by inversion of the hydrogel and contact with another culture surface. Similarly, VP-based materials on PMMA retain this property, allowing cell transplantation in a manner similar to the original hydrogel. After the transplant, it has been observed that the cultures retain good viability and continue their proliferative activity, reaching confluence at 7 days post-transplant.

5. Coating of Flat Polystyrene (PS) Substrates with VCL-Based Hydrogels and without Methacrylates. Its Use as Support for Cell Culture The hydrogel was prepared as in Example 2, except that PS was used instead of Nylon as the substrate, and brass sheets of 0.1 mm to make them as spacers, in addition to the materials indicated in Example 1. Both commercial thick PS plates and press prepared fine plates (0.5 mm) were evaluated.

Figure 11:
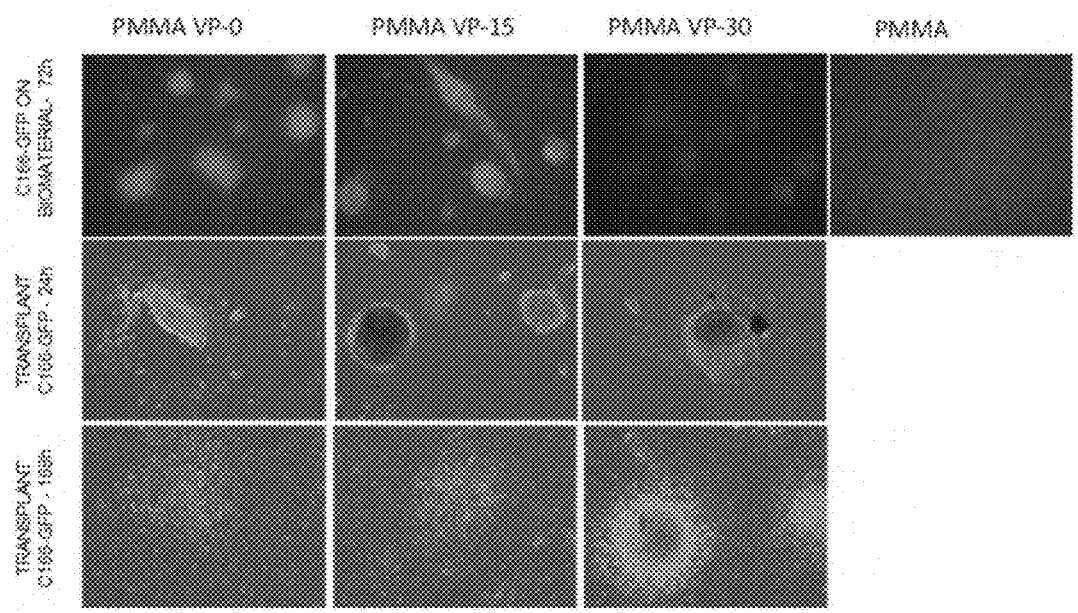
FIG. 11. PS sheets covered with thermosensitive hydrogel on a VCL base without methacrylate. a) Commercial coarse PS coating using a 0.5 mm silicone spacer. b) Commercial coarse PS coating prepared using a 0.1 mm brass spacer. c) Fine PS coating prepared using a 0.1 mm brass spacer.
Figure 12:
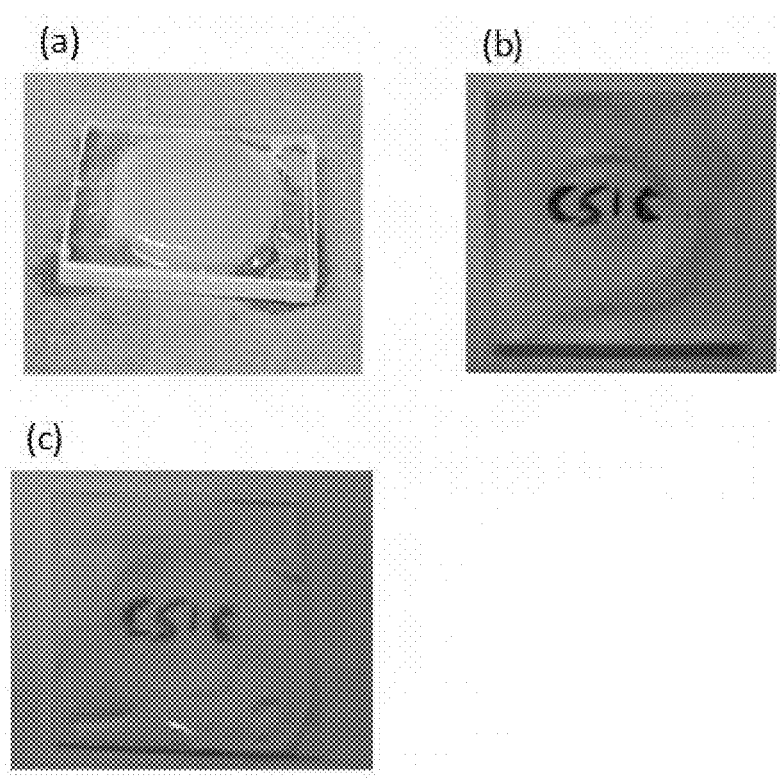
FIG. 12. Optical images of the surface of a 3 mm diameter cylinder after treatment with the solution that includes vinylpyrrolidone and sulfopropyl methacrylate potassium (molar ratio 6:1), as well as methacrylic and vinyl type crosslinking agents. The cylinder was immersed in the solution described above (polymerizable mixture described above (monomers, crosslinkers, photoinitiator and such, solvent optionally) and after a certain period of time (0, 15 or 30 min), the whole system was exposed to UV radiation for 30 minutes. Next, the cylinder was immersed in ethanol and the hydrogel was separated from the surface of the cylinder leaving a wrinkled surface with a thin superficial layer of hydrogel.
Figure 13:
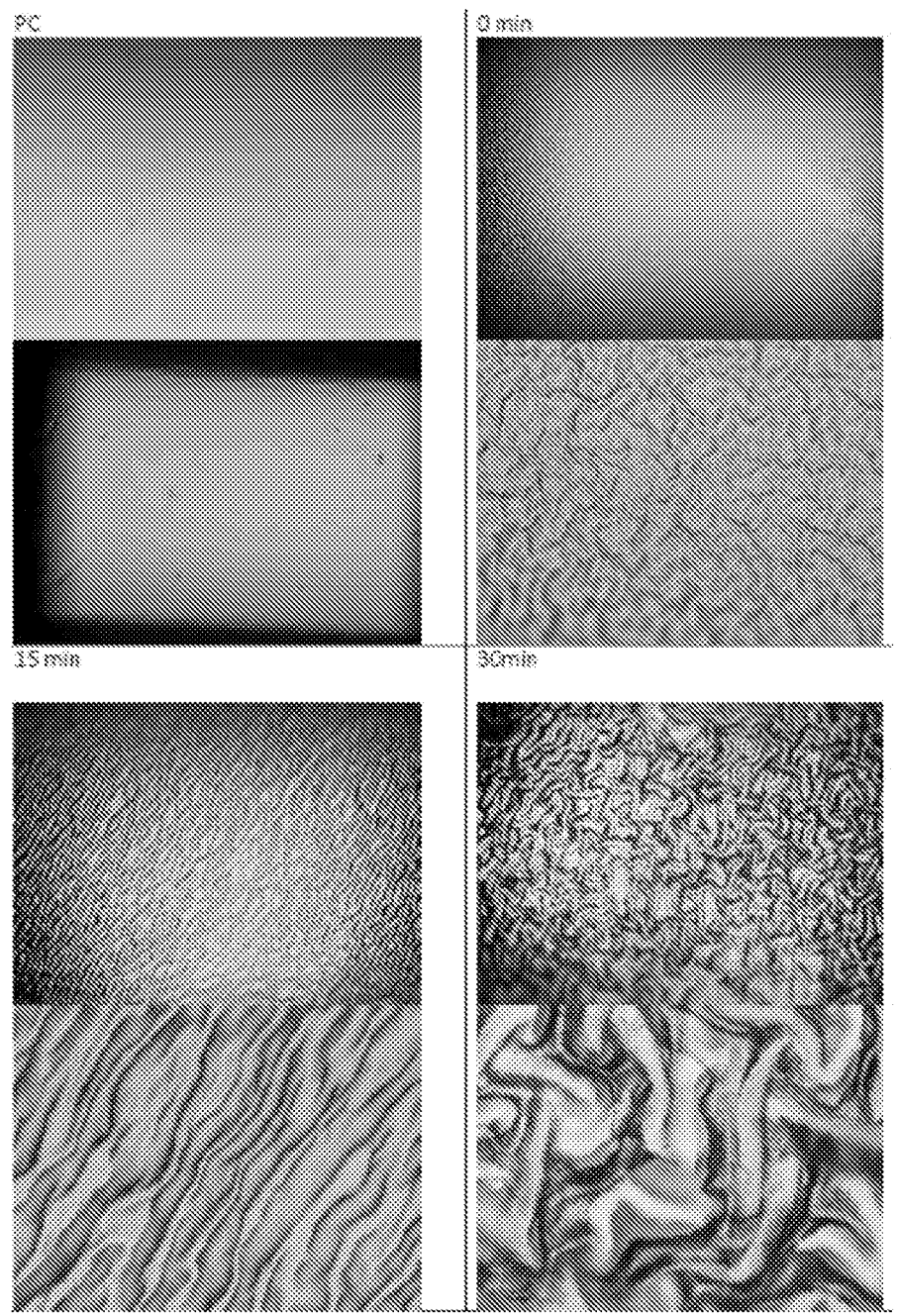

Solvent-free control coatings (bulk polymerization) were also prepared. It was observed that stable coatings were obtained when using ethanol as solvent as well as in bulk polymerization. In FIG. 11, coatings obtained with different conditions are shown. The coating was stable during the swelling and deflation processes. The transparency of the coating depends on the use or not of solvent and the type of PS. The samples obtained with commercial PS plates and brass spacers were highly transparent.

They were evaluated as cell culture supports and behaved similarly to example 2.

6. Coating of Flat Polylactic Acid (PLA) Substrates, With VCL-Based Hydrogels and Without Methacrylates The coatings were prepared similarly to example 2, except that PLA was used instead of Nylon as the substrate. They were evaluated as cell culture supports in the same way as in example 2. In this case, growth on the material is optimal, rapidly forming a monolayer over the entire coating. The interface is similar to the previous ones in this example.

7. Wrinkled Micrometric Coatings on Non-Planar Substrates

In addition to the flat surfaces, the developed system allows the coating of curved and complex structures. As an example of embodiment, the piece chosen is a 3 mm diameter cylinder made of polycarbonate. The cylinder was immersed in a mixture solution of vinylpyrrolidone, sulfopropylmethacrylate (in 6/1 molar ratio) and dimethacrylate and divinyl type crosslinkers, and irradiated with UV-light for 30 min. The initiation of the photopolymerization process is performed instantaneously (previous contact time 0 min), as well as after 15 and after 30 min. As in the case of flat surfaces and shown in FIG. 10, the roughness increases with the contact time. In this case, the PC used and the chosen conditions give rise to the formation of wrinkles already occurs for short contact times (prior to photopolymerization).

The invention claimed is:
1. A product comprising:
   a) a polymeric substrate and
   b) a hydrogel based on vinyl-lactam type monomers, without methacrylates or with ionic methacrylates, and at least two crosslinkers,
   wherein there is an interface between the substrate and the hydrogel, the interface formed by a gradient of both the substrate and the hydrogel network, forming a semi-interpenetrated network structure.
2. The product according to claim 1, comprising:
   a) a polymeric substrate and one of:
   b) a hydrogel based on vinyl-lactam type monomers, without methacrylates, wherein the vinyl-lactam is vinylcaprolactam, the polymeric substrate is nylon, and the two crosslinkers are ethylene glycol dimethacrylate and 3,3'-(propyl)-di-1-vinyl-2-pyrrolidone, and
   b) a hydrogel based on vinyl-lactam type monomers, with ionic methacrylates, and at least two crosslinkers,
   wherein there is an interface between the substrate and the hydrogel, the interface formed by a gradient of both the substrate and the hydrogel network, forming a semi-interpenetrated network structure.
3. The product according to claim 1, comprising:
   a) a polymeric substrate and
   b) a hydrogel based on vinyl-lactam type monomers, with ionic methacrylates, and at least two crosslinkers,
   wherein there is an interface between the substrate and the hydrogel, the interface formed by a gradient of both the substrate and the hydrogel network, forming a semi-interpenetrated network structure.
4. The product according to claim 3, wherein the polymeric substrate is selected from a group consisting of polystyrene, polymethyl methacrylate, nylon, polycarbonate, polyvinyl chloride, polylactic acid and polycaprolactone.
5. The product according to claim 3, wherein the polymeric substrate is selected from a group consisting of nylon, polystyrene and polycarbonate.
6. The product according to claim 3, wherein the vinyl-lactam is selected from a group consisting of vinylcaprolactam and vinylpyrrolidone.
7. The product according to claim 6, wherein the vinyl-lactam is vinylcaprolactam.
8. The product according to claim 6, wherein the molar ratio vinyl-lactam/ionic methacrylate is in the range 2/1 to 100/1.
9. The product according to claim 3, wherein the ionic methacrylate is a cationic methacrylate selected from a group consisting of [2-(methacryloyloxy)alkyl]trimethylammonium salts, dimethylaminoethyl and diethylaminoethyl methacrylates.
10. The product according to claim 3, wherein the ionic methacrylate is a zwitterionic methacrylate selected from a group consisting of methacryloyloxyethyl phosphorylcholine and [3-(methacryloylamino)propyl]dimethyl(3-sulfopropyl) ammonium methacrylate hydroxide.

11. The product according to claim 3, wherein the ionic methacrylate is an anionic methacrylate selected from a group consisting of sulfoalkylmethacrylates salts.

12. The product according to claim 3, wherein the ionic methacrylate is a mixture of anionic methacrylate selected from a group consisting of sulfoalkyl methacrylates salts and cationic methacrylate selected from a group consisting of [2-(methacryloyloxy)alkyl]trimethylammonium salts.

13. The product according to claim 3, wherein the crosslinkers are selected from a group consisting of at least one of ethylene glycol di(meth)acrylate, triethylene glycol di(meth)acrylate, tetraethylene glycol di(meth)acrylate, trimethylolpropane tri(meth)acrylate, bisphenol A di(meth) acrylate, ethoxylate bisphenol A di(meth)acrylate, pentaerythritol tri-, and tetra(meth) acrylate, tetramethylene di(meth)acrylate, methylenebisacrylamide, methacryloxyethyl vinyl carbonate, triallylcyanurate, methacryloxyethyl vinyl urea, divinyl benzene, diallyl itaconate, allyl methacrylate, diallyl phthalate, polysiloxanylbisalkyl(meth)acrylate, polyethylene glycol di(meth)acrylate, vinyl methacrylate, divinyl adipate, divinylpyrrolidone derivatives, and 1,3-divinylimidazolin-2-one.

14. The product according to claim 13, wherein the crosslinkers are each present in concentrations in the range 0.1-10 moles % with respect to the moles of total monomers.

15. The product according to claim 13, wherein the crosslinkers are ethylene glycol di(meth)acrylate and 3,3'-(propyl)-di-1-vinyl-2-pyrrolidone.

16. The product according to claim 1, comprising:
a polymeric substrate that is nylon or polystyrene and
b) a hydrogel based on vinylpyrrolidone, VP, or vinylcaprolactam monomers and two crosslinkers that are ethylene glycol dimethacrylate and 3,3'-(propyl)-di-1-vinyl-2-pyrrolidone,
wherein there is an interface between the substrate and the hydrogel, the interface formed by a gradient of both the substrate and the hydrogel network, forming a semi-interpenetrated network.

17. The product according to claim 1, which is structured on its surface.

18. The product according to claim 17, which is structured on its surface by the formation of wrinkles.

19. A process to obtain the product defined in claim 1, wherein the process comprises at least the following steps:
a) mixing the vinyl-lactam type monomers and the at least two crosslinkers with a photoinitiator,
b) deposition of the mixture of (a) on the surface of the polymeric substrate and induction of photopolymerization under UV radiation and
c) swelling of the product obtained in (b) by immersion in water or in ethanol.

20. The process according to claim 19, wherein the polymeric substrate is selected from a group consisting of polystyrene, methyl polymethacrylate, nylon, polycarbonate, polylactic acid and polycaprolactone.

21. The process according to claim 19, wherein the polymeric substrate is one of nylon and polycarbonate.

22. The process according to claim 19, wherein the vinyl-lactam is selected from a group consisting of vinylcaprolactam and vinylpyrrolidone.

23. The process according to claim 19, wherein the vinyl-lactam is vinylcaprolactam.

24. The process according to claim 19, wherein the ionic methacrylate is a cationic methacrylate selected from a group consisting of [2-(methacryloyloxy)alkyl]trimethylammonium salts.

25. The process according to claim 19, wherein the ionic methacrylate is a zwitterionic methacrylate selected from a group consisting of methacryloyloxyethyl phosphorylcholine and [3-(methacryloylamino)propyl]dimethyl(3-sulfopropyl)ammonium methacrylate hydroxide.

26. The process according to claim 19, wherein the ionic methacrylate is an anionic methacrylate selected from a group consisting of sulfoalkylmethacrylates salts.

27. The process according to claim 19, wherein the crosslinkers are selected from a group consisting of ethylene glycol di(meth)acrylate, triethylene glycol di(meth)acrylate, tetraethylene glycol di(meth)acrylate, trimethylolpropane tri (meth)acrylate, bisphenol A di(meth)acrylate, ethoxylate bisphenol A di(meth)acrylate, pentaerythritol tri-, and tetra (meth)acrylate, tetramethylene di(meth)acrylate, methylenebisacrylamide, methacryloxyethyl vinyl carbonate, triallylcyanurate, methacryloxyethyl vinyl urea, divinyl benzene, diallyl itaconate, allyl methacrylate, diallyl phthalate, polysiloxanylbisalkyl(meth)acrylate, polyethylene glycol di(meth)acrylate, vinyl methacrylate, divinyl adipate, divinylpyrrolidone derivatives, and 1,3-divinylimidazolin-2-one.

28. The process according to claim 27, wherein the crosslinkers are ethylene glycol di(meth)acrylate and 3,3'-(propyl)-di-1-vinyl-2-pyrrolidone.

29. The process according to claim 19, wherein the UV radiation is maintained between 10 and 60 minutes.

30. The process according to claim 19, wherein the crosslinkers are used in a percentage comprised between 0.1% and 20% in moles with respect to the total monomer content.

31. The process according to claim 19, wherein the crosslinkers are each used in a percentage comprised between 0.1% and 10% in moles with respect to the total monomer content.

* * * * *